Oct. 28, 1969 W. FLEMER III Plant Pat. 2,935
YELLOW-WOOD TREE
Filed Dec. 5, 1967
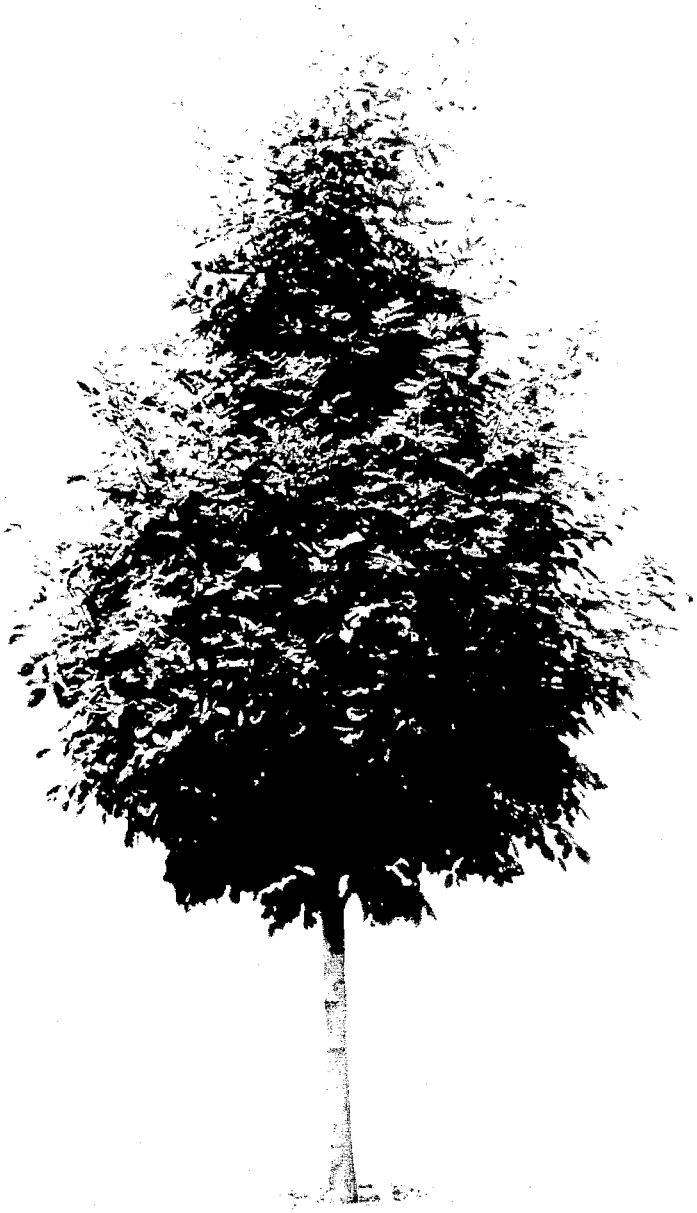
Inventor.
William Flemer, III
By: Robb & Robb
Attorneys.

United States Patent Office

Plant Pat. 2,935
Patented Oct. 28, 1969

2,935
YELLOW-WOOD TREE
William Flemer III, Princeton, N.J., assignor to Treesearch, Kingston, N.J., a partnership
Filed Dec. 5, 1967, Ser. No. 688,277
Int. Cl. A01h 5/12
U.S. Cl. Plt.—51 1 Claim The present invention relates to a new and distinct variety of yellow-wood tree of the species botanically known as *Cladrastis lutea,* which was originated by me as an intraspecific hybrid by crossing the variety of *Cladrastis lutea* known as "Griswold" (unpatented with the *Cladrastis lutea* variety known as "Perkins Institute Pink" (unpatented), the former being the seed parent and the latter being the pollen parent. The parent variety "Griswold" has never been introduced in commerce, but was named after the Griswold dormitory of the Lawrenceville School in Lawrenceville, N.J., where it originated. The name has never been published or registered with any varietal name register, but serves to identify its geographic origin. However, the parent variety "Perkins Institute Pink" is described on page 158 of the publication entitled "Trees for American Gardens" (1959 edition), by Dr. Donald Wyman.

As the result of this breeding, I have produced a new and improved yellow-wood tree which is distinguished from its parents, as well as from all other varieties of which I am aware, as evidenced by the following unique combination of characteristics which are outstanding therein:

(1) An exceptionally vigorous habit of growth which is about 4 times the normal growth rate when grafted on ordinary seedling understock commonly used;

(2) Exceptionally large flower panicles and individual flowers, both of which are substantially larger than those of ordinary seedling plants and one-third larger than those of both parent varieties; and (3) High resistance to leaf hopper feeding and folier mildew as compared with other seedling varieties grown under the same conditions.

Asexual reproduction of my new variety by bud-grafting, as performed by me in Plainsboro Township, N.J., shows that the foregoing characteristics and distinction come true and are established and transmitted through succeeding propagations.

The accompanying drawing shows a typical specimen tree of my new variety as depicted in black-and-white to illustrate its general form and habit of growth.

The following is a detailed description of my new variety, with color terminology in accordance with the Munsell Color Chart, except where general color terms of ordinary dictionary significance are obvious:

Parentage: Seedling.
*Seed parent.*—*Cladrastis lutea* "Griswold."
*Pollen parent.*—*Cladrastis lutea* "Perkins Institute Pink."

Propagation: Holds its distinguishing characteristics through succeeding propagations by bud-grafting.
Locality where grown and observed: South Brunswick Township, N.J.
Tree: Medium size; upright; dense; hardy.
*Trunk.* — Stocky; very smooth. Color — grey.
*Branches.*—Very stocky; smooth. Color—Chestnut Brown, Hue 7.5VR 3/2. *Lenticels.* — Abundant; small.
Foliage:
*Leaves.*—Abundant; dense; very large (35 cm. long and 24 cm. wide); singly compound; alternate leaflets; from 7 to 9 leaflets per leaf; thick. Color: upper surface—Dark Olive Green, Hue 5GY 3/2; lower surface—Light Green, Hue 5G 8/6. Margin—smooth edge. Petiole—medium length (4 cm. long). Glands—none. Stipules—none.
Flower buds: Concealed within leaf buds.
Flowers:
*Date of first bloom.*—May 25.
*Date of full bloom.*—June 1.
*Quantity.*—Abundant.
*Size.*—Large; borne in compound branched panicles, with 4 to 6 branches per panicle and from 65 to 75 flowers per panicle; panicles 38 cm. long and 14 cm. wide.
*Petalage.*—Number of petals—4. Shape of petals—pea-shaped. Size of petals—about 2.4 cm. long and 1.5 cm. wide.
*Color.*—Pure white, with yellow blotch in center corresponding to Vivid Yellow, Hue 7.5Y 8/12.
*Fragrance.*—Rich and fruity.
Fruit:
*Borne.*—During October.
*Abundance.*—Sparse.
*Size.*—In narrow pod, compressed between seeds; 3 or 4 seeds per pod.
*Color.*—Pale brown.
Insect and disease resistance: High resistance to leaf hopper feeding and foliar mildew, as determined by comparison with other varieties grown under the same conditions in New Jersey.

I claim:

1. A new and distinct variety of yellow-wood tree, substanially as therein shown and described, characterized particularly as to novelty by the unique combination of an exceptionally vigorous habit of growth which is about 4 times the normal growth rate when grafted on ordinary seedling understock commonly used, exceptionally large flowers panicles and individual flowers, both of which are substantially larger than the size of those of ordinary seedling plants and one-third larger than those of both parent varieties, and high resistance to leaf hopper feeding and foliar mildew as compared with other seedling varieties grown under the same conditions.

No references cited.

ROBERT E. BAGWILL, Primary Examiner